United States Patent [19]

Shimizu et al.

[11] Patent Number: 5,425,726
[45] Date of Patent: Jun. 20, 1995

[54] ABSORBENT ARTICLE

[75] Inventors: Shiggeyuki Shimizu; Harumitsu Toyoda; Masamichi Senoo; Keiji Abe, all of Tochigi, Japan

[73] Assignee: Kao Corporation, Tokyo, Japan

[21] Appl. No.: 301,723

[22] Filed: Sep. 7, 1994

Related U.S. Application Data

[63] Continuation of Ser. No. 58,667, May 10, 1993, abandoned, which is a continuation of Ser. No. 825,329, Jan. 27, 1992, abandoned, which is a continuation of Ser. No. 470,699, Jan. 26, 1990, abandoned.

[30] Foreign Application Priority Data

Feb. 8, 1989 [JP] Japan ................................ 1-29390

[51] Int. Cl.6 .......................................... A61F 13/15
[52] U.S. Cl. ............................ 604/385.1; 604/385.2; 604/378
[58] Field of Search .................. 604/395, 400, 385.1, 604/385.2, 378

[56] References Cited

U.S. PATENT DOCUMENTS

| | | | |
|---|---|---|---|
| 1,695,153 | 12/1928 | Nelson | 604/400 X |
| 1,989,283 | 1/1935 | Limacher | 604/385.1 X |
| 2,492,620 | 12/1945 | Cohen | 604/395 |
| 2,541,629 | 2/1951 | Woods | 604/400 |
| 2,793,642 | 5/1957 | Andruhovici | 604/400 X |
| 3,842,838 | 10/1974 | Gellert . | |
| 3,874,385 | 4/1975 | Gellert . | |
| 3,921,638 | 11/1975 | Schaar . | |
| 4,022,212 | 5/1977 | Lovison | 604/395 |
| 4,114,621 | 9/1978 | Mims | 604/395 |
| 4,662,877 | 5/1987 | Williams | 604/385.2 |
| 4,731,071 | 3/1988 | Pigneul | 604/385.1 |
| 4,790,839 | 12/1988 | Ahr | 604/385.1 X |
| 4,808,176 | 2/1989 | Kielpikowski | 604/385.2 |
| 4,808,177 | 2/1989 | Des Marais et al. | 604/385.1 |
| 4,961,736 | 10/1990 | McCloud | 604/385.1 |
| 4,990,147 | 2/1991 | Freeland | 604/385.2 |
| 5,007,906 | 4/1991 | Osborn et al. | 604/385.1 |

FOREIGN PATENT DOCUMENTS

| | | | |
|---|---|---|---|
| 0335253 | 10/1989 | European Pat. Off. | 604/400 |
| 0359410 | 3/1990 | European Pat. Off. . | |
| 661113 | 7/1929 | France . | |
| 53-26175 | 7/1978 | Japan . | |
| 54-29932 | 9/1979 | Japan . | |
| 58-18520 | 2/1983 | Japan . | |
| 59-53702 | 3/1984 | Japan . | |
| 2161059 | 1/1986 | United Kingdom . | |
| 2232600 | 12/1990 | United Kingdom | 604/378 |

*Primary Examiner*—David H. Willse

[57] ABSTRACT

An absorbent article such as a disposable diaper, effective to prevent liquid from leaking, comprises a liquid-impermeable back sheet, a liquid-permeable top sheet, an absorbent provided between the back sheet and the top sheet and a liquid-permeable surface sheet fixed on the top sheet at both ends of the surface sheet at the longitudinal direction of the article, but not fixed thereto at the intermediate part.

7 Claims, 1 Drawing Sheet

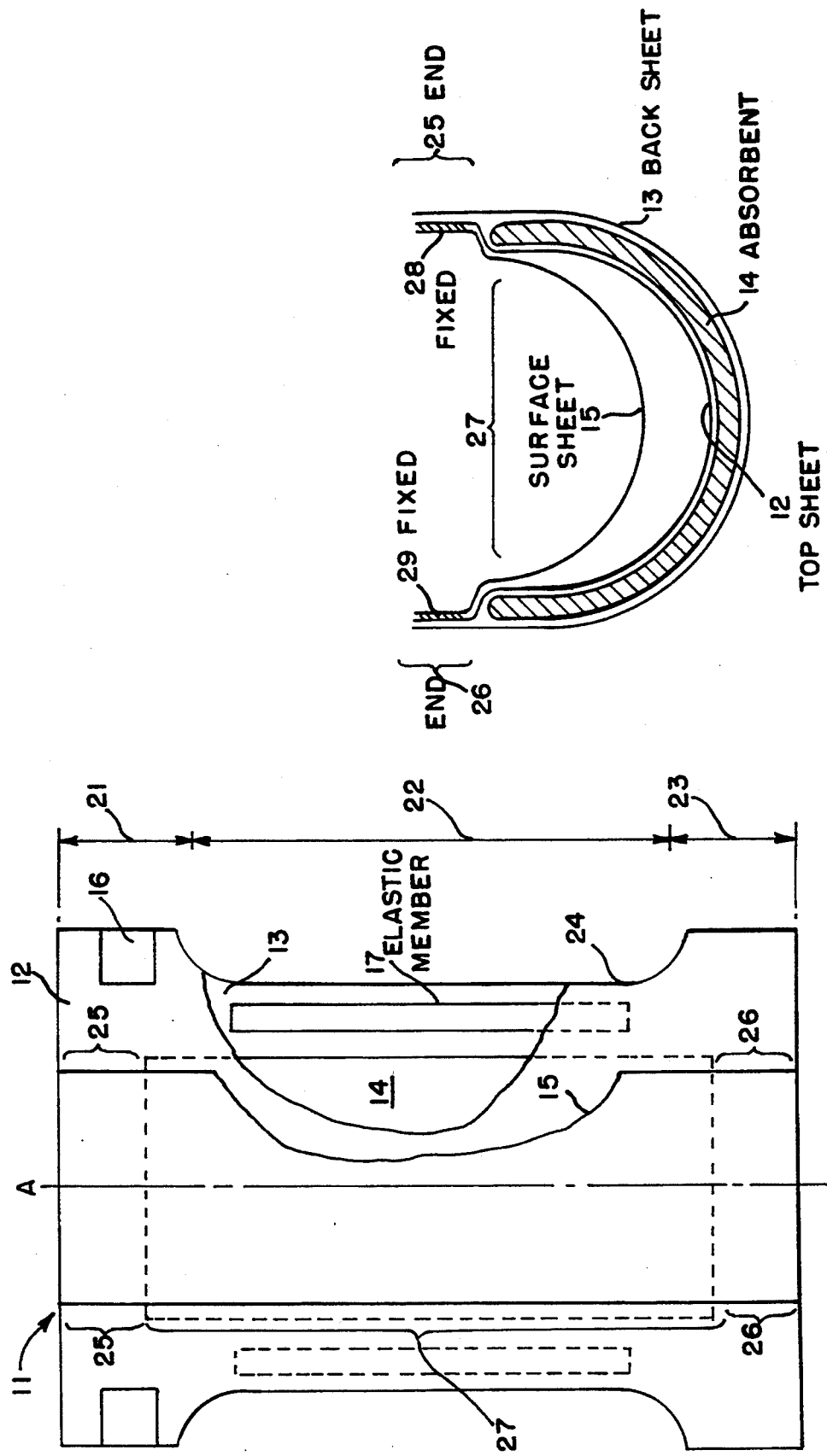

ABSORBENT ARTICLE

This application is a continuation of application Ser. No. 08/058,667 filed on May 10, 1993, which is a Jan. 27, 1992, which is a continuation of application Ser. No. 07/470,699 filed Jan. 26, 1990, all now abandoned.

The present invention relates to an absorbing article such as a disposable diaper, and more particularly, to an absorbing article provided with an upper sheet for leakage prevention and improved absorbing performance.

PRIOR ART

The major function of an absorbing article such as a disposable diaper is to absorb the wearer's excreta without permitting them to soil any articles (such as clothing) in contact with the wearer.

A prior disposable diaper is provided with an elastic member at its sideflaps extending from the side ends of the absorber to prevent the liquid from leaking out because the side flaps may come into close contact with the wearer's crotch by the elastic function of the elastic member. Japanese Utility Model Publication A No. 58-18520 and Japanese Patent Publication A No. 58-53702 show that the side flaps have a pocket or an antileakage wall.

The conventional absorbing article such as a disposable diaper is usually constructed such that the liquid-permeable sheet placed on the absorber is fixed to the absorber. A disposable diaper as disclosed in Japanese Patent Publication No. 26175/1978 has a laminated structure so that the liquid-permeable top sheet is peeled off to dispose of wastes easily. A disadvantage of this disposable diaper is that because the top sheet is being fixed over its entire surface, the top sheet in contact with the wearer's skin does not follow the wearer's movement but is liable to get out of contact with the wearer's skin. A disposable diaper as disclosed closed in Japanese Patent Publication No. 29932/1979 has an inner sheet which is constructed such that the central part can be separated and disposed of together with wastes. This disposable diaper also has the same disadvantage as mentioned above because the inner sheet is fixed along the entire periphery of the liquid-absorbing pad.

There has been no absorbing article which is constructed such that the liquid-permeable sheet placed on the absorber is fixed at both of its ends to the absorber, or to the surface sheet, or to the liquid-impermeable back sheet, with its intermediate part unfixed over its entire width.

The conventional absorbing article such as a disposable diaper is provided with elastic side flaps to prevent the leakage of excreta such as urine and feces. The side flaps are connected to the absorber. The absorbing article also has an absorber which is deformed comparatively easily, and the deformed absorber is liable to separate from the wearer's crotch. When the absorber separates from the wearer's crotch, the flaps arranged on the sides of the absorber follow the movement of the absorber and hence separate from the wearer's crotch, with the result that the flaps lose their function to prevent leakage. When the absorber is separate from the wearer's crotch, it will not be able to absorb even a small quantity of excreta.

SUMMARY OF THE INVENTION

It is an object of the present invention to provide an absorbing article which is free of the above-mentioned disadvantage that the absorber separates from the wearer's crotch, permitting the wearer's excreta to leak. The absorbing article of the present invention is constructed such that even when the absorber separates from the wearer's crotch, it does not permit the wearer's excreta to leak.

To achieve this object, the present inventors carried out extensive research which led to the finding that a liquid-permeable sheet remains in close contact with the wearer's crotch if it is placed on the top sheet above the absorber, with both of its ends in the lengthwise direction fixed and its intermediate part unfixed. The present invention was completed on the basis of this finding.

The gist of the present invention resides in an absorbing article of the type having a liquid-impermeable back sheet, a liquid-permeable top sheet, an absorber placed between said two sheets, and a liquid-permeable upper sheet placed on said top sheet, characterized in that said upper sheet is placed with, both of its in the lengthwise direction fixed and its intermediate part unfixed.

The invention provides an absorbent article which comprises a liquid-impermeable back sheet, a liquid-permeable top sheet, an absorbent provided between the back sheet and the top sheet and a liquid-permeable surface sheet fixed on the top sheet at both ends of the surface sheet at the longitudinal direction of the article, but not fixed thereon at the intermediate part.

It is preferable that the surface sheet is shorter than the top sheet at the longitudinal direction of the article when it is not used.

It is also preferable that the surface sheet has the central part which may fall downward from the peripheral part when it has a weight of 40 grams on the central part.

It is preferred that at least the peripheral part of the surface sheet comprises an elastic material. The surface sheet may be composed totally of an elastic material. Alternatively it may have an elastic member such as an elastic strip, in particular on the side ends thereof.

It is preferable that the peripheral part of the surface sheet is positioned above the peripheral part of the article when it is not used. The surface sheet may be made of a liquid-impermeable material such as nonwoven fabric, film and net.

The absorber may consist of flap pulp which preferably contains a superabsorbent polymer such as starch, cellulose, synthetic polymers, a graft-copolymer of starch and acrylic acid or a salt thereof, a saponified product of a graft copolymer of starch and acrylonitrile, a crosslinked product of sodium carboxymethylcellulose and a polymer of acrylic acid or a salt thereof, which can afford absorption of liquid 20 times or more of its weight, thereby forming a gel.

The top sheet may be composed of nonwoven fabrics, film or net, being liquid-permeable. It preferably is water-repellent at its peripheral part and permeable at the central part.

The back sheet is preferably composed of a low density polyethylene sheet having a thickness of 10 to 60 microns, more preferably being porous to allow much humidity to dissipate.

The elastic member may be composed of polyurethane, natural rubber or fibers which are shrinkable when they are wetted with water.

The absorbing article of the present invention is constructed such that the liquid-permeable upper sheet is placed on the top sheet above the absorber, with both of its ends in the lengthwise direction fixed to the absorber, or the liquid-permeable top sheet, or the liquid-impermeable back sheet, and its intermediate part unfixed over its entire width. Therefore, the intermediate part of the liquid-permeable upper sheet easily comes into close contact with the wearer's crotch without being affected by the deformation of the absorber.

The absorbing article of the present invention denotes a disposable diaper or the like to absorb excreta. In this invention, the absorbing article is not limited to the diaper which is worn by babies and incontinent patients; but it may also be applied to briefs for incontinent patients.

The absorbing article of the present invention effectively absorbs the wearer's excreta (urine and feces) and prevents their leakage, because it is constructed such that the intermediate part of the liquid-permeable upper sheet is not fixed to the absorber and hence it comes into close contact with the wearer without being affected by the deformation of the absorber.

The absorbing article of the present invention absorbs the wearer's excreta in the following manner. Excreta are received by the intermediate part of the liquid-permeable upper sheet and then absorbed by the absorber. The intermediate part of the liquid-permeable upper sheet comes into close contact with the wearer's crotch when the diaper is worn, so that it receives the wearer's excreta almost completely without leakage and introduces them to the center of the absorber, permitting the absorber to fully exhibit its absorbing performance.

The free intermediate part of the liquid-permeable upper sheet works together with the absorber in the following manner. Since the absorber is under the intermediate part of the liquid-permeable upper sheet, it absorbs the excreta received by the intermediate part of the liquid-permeable upper sheet. In some embodiments, the intermediate part of the liquid-permeable upper sheet comes into contact with the top sheet, so that the excreta received by the intermediate part are rapidly introduced to the absorber via contact points.

The important effect of the present invention is the ability of the diaper to receive the wearer's excreta almost completely without leakage and to introduce them to the center of the absorber, thereby making full use of the absorbing performance, which is attributed to the fact that the liquid-permeable upper sheet has the intermediate part which almost independently comes into close contact with the wearer's crotch. In addition, the diaper of the present invention can hold solid excreta such as feces without leakage. Another effect of the present invention is the ability of the liquid-permeable upper sheet to be easily removed from the diaper proper so that it can be discarded together with excreta, which is attributed to the fact that the liquid-permeable upper sheet is fixed at its ends with a limited amount of fixing force.

BRIEF DESCRIPTION OF THE DRAWINGS

The accompanying drawings show an embodiment of the absorbing article of the present invention. FIG. 1 is an expanded plan view of the diaper, with a part cut away. FIG. 2 is a sectional view of the diaper in worn state, taken along the line A—A of FIG. 1.

11 ... Diaper
12 ... Top sheet
13 ... Back sheet
14 ... Absorber
15 ... Upper sheet
16 ... Tape fastener
17 ... Elastic body
21 ... Back waist part
22 ... Crotch part
23 ... Front waist part
24 ... Side flap
25 ... End
26 ... End
27 ... Free part
28 ... Fixing means
29 ... Fixing means In the natural configuration which the diaper of the invention has before the use, L1 is a length at the longitudinal direction of the surface sheet and L2 is a length at the longitudinal direction of of the top sheet. It is preferable that $0.3L_2 \leq L_1 \leq 0.98L_2$, more preferably $0.5L2 \leq L1 \leq 0.90L2$. When $L_1$ is smaller than 0.3 of $L_2$, the diaper will become much less fit for a wearer. When $L_1$ is larger than 0.98 of $L_2$, the space between the surface sheet and the top sheet will be too small to provide the advantage effectively.

The preferred embodiment of the present invention will be described in more detail with reference to the accompanying drawings. Although the following description of the preferred embodiment is based on a disposable diaper, the scope of the present invention is not restricted to it.

EXAMPLE 1

A disposable diaper pertaining to the present invention is shown in FIG. 1 which is an expanded plan view, with a part cut away for the illustration of the structure, and with the side that comes into contact with the wearer upward.

As shown in FIG. 1, a disposable diaper 11 is made up of a liquid-impermeable back sheet 13, a liquid-permeable top sheet 12, an absorber 14, and a liquid-permeable upper sheet 15. It consists of a back waist part 21, a front waist part 23, and a crotch part 22, and it has side flaps 24. In addition, it may optionally have a pair of tape fasteners 16 and a pair of elastic bodies 17 within the side flaps, which will improve the function and performance of the diaper.

According to this structure of the diaper 11, the absorber 14 is placed between the liquid-impermeable back sheet 13 and the liquid-permeable top sheet 12, and the liquid-permeable upper sheet 15 is placed on the liquid-permeable top sheet 12. According to a more desirable embodiment, the optional elastic bodies 17 are placed between the back sheet 13 of the side flap 24 and the top sheet 12 of the side flap 24, and the paired tape fasteners 16 are fixed to the back waist part 21 of the side flap 24.

The diaper 11 is elongated in its lengthwise direction. The back sheet 13 and the top sheet 12 have almost the same length and width. The backsheet 13 is usually made of a low-density opaque polyethylene sheet having a thickness of 10μm to 60μm. It should preferably be a porous sheet which is permeable to water vapor but is impermeable to liquids. Moreover, the porous sheet should preferably be one which makes as small a rustling noise as possible when crumpled. The top sheet 12 is usually made of a nonwoven fabric having a basis weight of 15–40 g/m². It should preferably have a Hater-repellent periphery and a hydrophilic central part.

The elastic body 17 is usually made of polyurethane rubber or natural rubber in the form of a string or ribbon. Each elastic body 17 consists of 1 to about 5 rubber strings or ribbons. The length of the elastic body 17 is about 30% to 60% of the length of the diaper. The elastic body 17 should be stretchable from about 1.3 to about 2.0 times its free length.

The absorber 14 is usually a pad of crushed softwood kraft pulp covered by water-absorbing paper. It should preferably contain a polymeric absorber. The pad usually weighs about 10 g to 40 g.

The liquid-permeable upper sheet 15 is placed on the top sheet 12. It is fixed to the above-mentioned top sheet 12 at both ends 25 and 26 of the diaper in its lengthwise direction, with its intermediate free part 27 unfixed. The width of the upper sheet 15 should preferably be about 30% to about 70% of the width of the diaper 11. Especially, it should be narrower than the minimum width of the crotch section 22 of the absorber 14. This makes better use of the absorber 14. The length of the upper sheet 15 may not equal that of the diaper 11 but should preferably be shorter substantially shorter. The flat shape of the upper sheet 15 should preferably be such that the width of the free part 27 is narrow and the width of the ends 25 and 26 is wide so that the upper sheet 15 comes into close contact with the wearer's crotch. However, there could be an instance where the free part 27 is as wide as or wider than the ends 25 and 26. The upper sheet 15 may be made of a nonwoven fabric, reticulated sheet, porous sheet, or elastic sheet which is permeable to liquids.

When worn, the diaper has a shape as shown in FIG. 2 which is a sectional view taken along the line A—A of FIG. 1. The liquid-permeable upper sheet 15 is fixed to the liquid-permeable top sheet 12 by fixing means 28 and 29 at the ends 25 and 26, but the free part 27 is not fixed. The length of the free part 27 should preferably be substantially shorter than the distance between the inner ends of the fixing means 28 and 29 when the diaper is stretched flat. With these dimensions, the free part 27 separates from the absorber 14, as shown in FIG. 2. The fixing means 28 and 29 should be at two positions in the lengthwise direction of the diaper 11 and they should also be at the position where the free part 27 exists. The preferred position is within the range of from about 10 mm to about 50 mm from the front and rear ends in the length-wise direction of the diaper 11. The width of the fixing means 28 and 29 should preferably be close to the front width of the upper sheet 15. The area of the fixing means 28 and 29 is not specifically limited. The peel strength of the top sheet 12 and upper sheet 15 at the fixing means 28 and 29 should be such that the upper sheet 15 does not peel off while the diaper is worn but can be peeled off without any loss of strength when it is to be peeled off for the disposition of excreta. The specific fixing means 28 and 29 include hot-melt bonding, heat bonding, ultrasonic bonding, sewing, and hook-loop combination.

In the embodiment shown in FIGS. 1 and 2, the liquid-permeable upper sheet 15 is placed on the liquid-permeable top sheet 12 and the top sheet 12 is arranged all over the diaper 11. However, it is not necessary that the top sheet 12 should exist under the entire area of the upper sheet 15. In this case, the fixing means 28 and 29 of the upper sheet 15 are partly tied up with the back sheet.

Comparative Example 1.

A disposable diaper used here consists of a liquid-permeable top sheet, a liquid-inpermeable back sheet, and an absorber.

EXAMPLE 2

A diaper used here is the same diaper as used in Comparative Example 1 except further comprising a surface sheet composed of hydrophilic nonwoven fabric produced by melting polyolefine fiber.

EXAMPLE 3

The same diaper as used in Comparative Example 1 further comprises a surface sheet of nonwoven fabric of rayon produced by water-needling.

EXAMPLE 4

The same diaper as used in Comparative Example 1 further comprises a surface sheet of composed of a polyolefine net.

Comparative Example 2

The same diaper as used in Comparative Example 1 further comprises a surface sheet of heavy duty polyvinyl chloride having perforations of 5 mm diameter at intervals of 10 mm.

EXAMPLE 5

The same diaper as used in Comparative Example 1 further comprises a surface sheet of heat-fused polyolefin fiber, being shorter at the longitudinal direction than the top sheet.

EXAMPLE 6

The same diaper as used in Comparative Example 1 further comprises a surface sheet of heat-fused polyolefin fiber, being shorter at the longitudinal direction than the top sheet, being provided with an elastic member of natural rubber at the peripheral part.

In order to list the antileakage property, the above obtained diapers were tested with a model imitating a baby weighing 10 kg. Ten grams of a test liquid at a time were repeatedly injected thereinto until the liquid had been found to leak. Results are shown in terms of the amount of the liquid absorbed until the leaking at the back when the model was placed in supine position and then at the front, in ortostatic position.

| injection rate | Amount of leakage | Comp. Ex. 1 | Ex. 2 | Ex. 3 | Ex. 4 |
|---|---|---|---|---|---|
| 3 g/second | the back | 30 | 60 | 50 | 50 |
|  | the front | 30 | 60 | 50 | 50 |
| 5 g/second | the back | 30 | 50 | 40 | 40 |
|  | the front | 30 | 50 | 40 | 40 |
| 8 g/second | the back | 20 | 50 | 40 | 40 |
|  | the front | 20 | 50 | 40 | 40 |

| injection rate | amount of leakage | Comp. Ex. 2 | Ex. 5 | Ex. 6 |
|---|---|---|---|---|
| 3 g/second | the back | 30 | 50 | 60 |
|  | the front | 30 | 50 | 60 |

What is claimed is:

1. An absorbent article having a front waist portion, a back waist portion and a crotch portion comprising:
   a liquid impermeable backsheet;

a liquid permeable top sheet of a shape and size corresponding to a shape and size of said backsheet;

an absorbent member provided between the back sheet and the top sheet; and a liquid permeable surface sheet of a continuous uninterrupted material lying over and spaced apart from and having a width less than a width of said top sheet, wherein said back sheet and said top sheet hold said absorbent member therebetween and said surface sheet is fixed only to opposing longitudinal ends of said top sheet within the waist portions of said absorbent article.

2. The article as claimed in claim 1, in which a central part of the surface sheet may fall downward from a peripheral part when it has a weight of 40 grams on the central part.

3. The article as claimed in claim 2, in which the peripheral part of the surface sheet comprises an elastic material.

4. The article as claimed in claim 2, in which the peripheral part of the surface sheet is spaced apart from a peripheral part of the top sheet when it is not used.

5. The article as claimed in claim 1 in which the length of the surface sheet is from 0.5 to 0.9 times the length of the top sheet.

6. The article as claimed in claim 1 and further comprising an elastic member in a peripheral part of the back sheet.

7. The absorbent article according to claim 1, wherein said liquid permeable surface sheet has a length of 0.3–0.98 times the length of said top sheet in longitudinal direction of the article when it is not used.

* * * * *